(12) United States Patent
Bartoli et al.

(10) Patent No.: US 8,785,664 B2
(45) Date of Patent: *Jul. 22, 2014

(54) PROCESS FOR THE PREPARATION OF NEBIVOLOL

(71) Applicant: Menarini International Operations Luxembourg S.A., Luxembourg (LU)

(72) Inventors: Sandra Bartoli, Pomezia (IT); Amalia Cipollone, Rome (IT); Daniela Fattori, Velletri (IT)

(73) Assignee: Menarini International Operations Luxembourg S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 13/907,677

(22) Filed: May 31, 2013

(65) Prior Publication Data

US 2013/0274486 A1    Oct. 17, 2013

Related U.S. Application Data

(63) Continuation-in-part of application No. 13/578,018, filed as application No. PCT/EP2011/051876 on Feb. 9, 2011, now Pat. No. 8,487,122.

(30) Foreign Application Priority Data

Feb. 11, 2010  (IT) .............................. RM2010A0053

(51) Int. Cl.
*C07D 311/00* (2006.01)

(52) U.S. Cl.
USPC .......................................................... 549/407

(58) Field of Classification Search
CPC ............................ C07D 407/12; C07D 311/58
USPC ....................................................... 549/407
See application file for complete search history.

(56) References Cited

U.S. PATENT DOCUMENTS

| | | | |
|---|---|---|---|
| 4,654,362 A | 3/1987 | Van Lommen et al. | |
| 6,545,040 B1 | 4/2003 | Xhonneux et al. | |
| 7,560,575 B2 | 7/2009 | Bader et al. | |
| 8,487,122 B2 * | 7/2013 | Bartoli et al. | 549/407 |
| 2007/0259950 A1 | 11/2007 | Sheth et al. | |
| 2010/0076206 A1 | 3/2010 | Ullucci et al. | |
| 2012/0316351 A1 | 12/2012 | Bartoli et al. | |

FOREIGN PATENT DOCUMENTS

| | | |
|---|---|---|
| EP | 0334429 | 9/1989 |
| EP | 1741712 | 1/2007 |
| WO | 2008/064826 | 6/2008 |

OTHER PUBLICATIONS

Chandrasekhar et al. "Enantioselective total synthesis of the antihypertensive agent (S,R,R,R)-Nebivolol" *Tetrahedron*, vol. 56, No. 34, pp. 6339-6344 (Aug. 2000).

Int'l Search Report for PCT/EP2011/051876, four pages, dated Mar. 9, 2011.

* cited by examiner

*Primary Examiner* — Nizal Chandrakumar

(74) *Attorney, Agent, or Firm* — Nixon & Vanderhye PC

(57) ABSTRACT

The present invention relates to a novel process for the synthesis of Nebivolol product represented in Scheme (1), comprised of a reduced number of high-yield steps, and characterized by the kinetic resolution of the two epoxide pairs diastereoisomeric therebetween (mixture 1), allowing to avoid complex chromatographic separations.

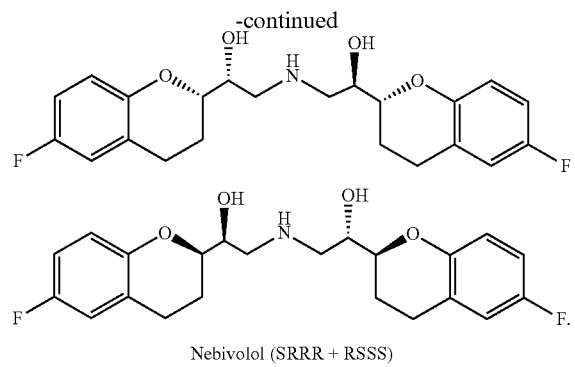
Nebivolol (SRRR + RSSS)
7 Claims, No Drawings

PROCESS FOR THE PREPARATION OF NEBIVOLOL

This application is a Continuation-In-Part of application Ser. No. 13/578,018, filed Aug. 9, 2012, now allowed; which is the U.S. national stage of Application No. PCT/EP2011/051876, filed Feb. 9, 2011; the entire contents of each of which are hereby incorporated by reference.

FIELD OF THE INVENTION

The present invention relates to a novel process for the synthesis of Nebivolol. Nebivolol is a racemic mixture of the two enantiomers [2S[2R[R[R]]]] α,α'-[imino-bis(methylene)]bis[6-fluoro-chroman-2-methanol] and [2R[2S[S[S]]]] α,α'-[imino-bis(methylene)]bis[6-fluoro-chroman-2-methanol] (Scheme 2).

In particular, it is reported the kinetic resolution of the two diastereoisomeric pairs of RS/SR and SS/RR epoxides (scheme 1, mixture 1) by treatment with an amine in a suitable solvent.

Scheme 2

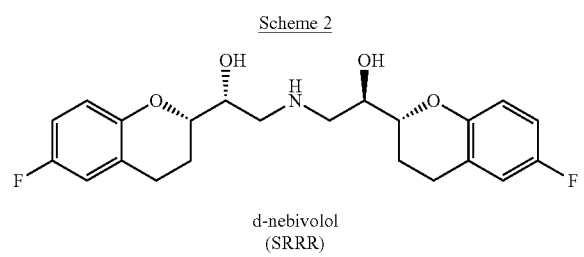

d-nebivolol
(SRRR)

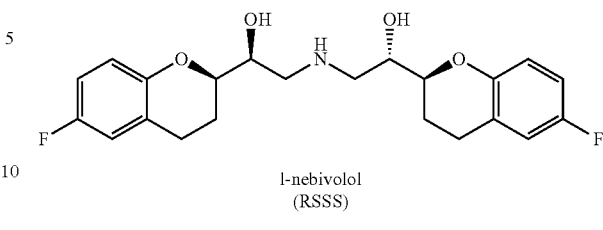

l-nebivolol
(RSSS)

Nebivolol

STATE OF THE ART

Nebivolol is known as an adrenergic beta-receptor antagonist, an antihypertensive agent, a platelet aggregation inhibitor and a vasodilating agent.

Nebivolol has basic properties and may be converted into an acceptable pharmaceutical salt form by treatment with an acid. The hydrochloride salt is the marketed form.

Nebivolol contains four asymmetric centres, and therefore 16 stereoisomers are theoretically possible. However, because of the particular structure of the molecule (the presence of an axis of symmetry), only 10 stereoisomers can actually be formed (Scheme 3).

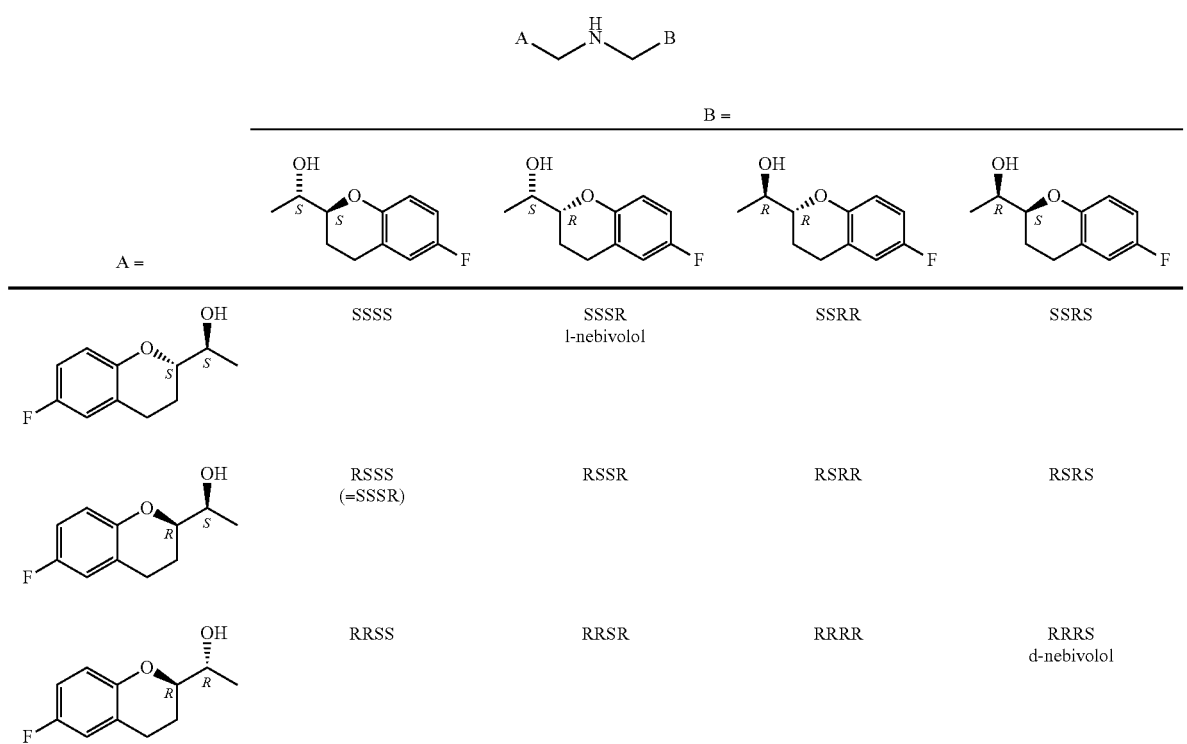

Scheme 3. Possible stereoisomers for nebivolol

Scheme 3. Possible stereoisomers for nebivolol

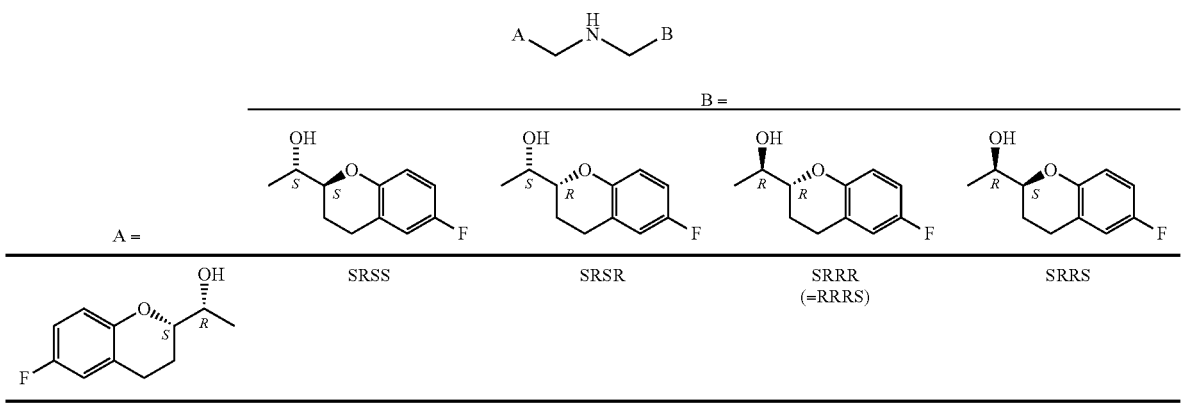

In fact, because of the symmetry of the molecule, RSSS=SSSR, RRSS=SSRR, SRSS=SSRS, RRSR=RSRR, SRSR=RSRS and RRRS=SRRR.

U.S. Pat. No 4,654,362 (EP 0145067, Janssen) describes the preparation of Nebivolol with use of epoxide isomers (Scheme 1, mixture 1: RS, SR, RR and SS) as key intermediates in the synthesis. These are separated, with a chromatography column, into the two epoxide racemates (RS/SR) and (RR/SS).

EP 334429 (Janssen) describes the same process reported in EP 0145067, but with more experimental details. EP 0334449 describes a stereoselective synthesis of the isomer [2R, αS, 2'S, α'S]-α,α'-[iminobis(methylene)]bis[6-fluoro-3,4-dihydro-2H-1-benzopyran-2-methanol].

WO 2006/016373 (Hetero Drugs Limited) describes fractional crystallization methods applied at the level of the diastereoisomeric mixture of benzyl nebivolol in the form of hydrochloride salt, but is silent on epoxide opening or separation methods (compound 1).

Also WO 2006/025070 (Torrent Pharmaceutical) remains within the classical synthesis described by U.S. Pat. No. 4,654,362 and merely introduces a method of separation of the diastereoisomeric pairs at the level of benzyl nebivolol in the form of hydrochloride salt. In the subsequent WO 2007/083318 it is claimed the use of diisopropyl ether for the crystallization of benzyl Nebivolol intermediate as free base.

WO 2007/041805 (Egis GyOgyszergyar) describes a process for the preparation of [2S*[R*[R*[R*]]]] and [2R*[S*[S*[S*]]]]-(±)-α,α'-[iminobis(methylene)]bis[6-fluoro-3,4-dihydro-2H-1-benzopyran-2-methanol] and its individual pure [2S*[R*[R*[R*]]]] and [2R*[S*[S*[S*]]]] enantiomers starting from very different compounds.

In WO 2008/010022 (Cimex Pharma) and WO 2008/064826 (Zach System) other synthetic methods are advanced, in which however more or less complex procedures for isomer separation have to be provided for.

WO 2008/064827 describes the separate and enantioselective synthesis of d- and l-Nebivolol.

On the basis of literature evidence available to date, Nebivolol synthesis still entails numerous synthetic problems. The original Janssen synthesis going through the epoxides (Scheme 1, mixture 1) is surely the shorter one, but requires a separation by preparative HPLC of the two diastereoisomeric epoxide pairs. The other methods generally envisage many more synthetic steps.

Therefore, the need to develop a novel synthetic process, suitable for industrial use and possibly avoiding the use of preparative HPLC though maintaining a limited number of synthetic steps, is markedly felt.

SUMMARY OF THE INVENTION

It has now surprisingly been found a more effective process for the synthesis of Nebivolol, which is summarized in Scheme 1. This process allows to eliminate the drawbacks highlighted hereto for the synthesis routes previously known, i.e., it:

a) avoids separation by preparative HPLC of the pairs (4RR/SS RS/SR) of epoxides enantiomers).

b) does not envisage the separate and parallel synthesis of the various enantiomers.

The reaction of the mixture 1 with an amine in primary alcohols such as methanol, ethanol, propanol, etc., proceeds quickly and cleanly, but almost without any diastereoselectivity, i.e. the two pairs of epoxides contained in 1, (SR+RS) and (RR+SS) exhibit very similar reaction velocities. From studies reported in the literature [Can. J. Chem. (1967), 45, 1597-1600] it seems that the role of alcohol in the opening of epoxides by an amine is not merely that of a solvent, but also of providing acid catalysis.

By conformational analysis studies, we were able to prove that the two epoxides have different conformational preferences. Consequently, a specific interaction with an alcohol can be influenced by the steric hindrance of the alcohol itself. Surprisingly, we demonstrated that by using sterically hindered alcohols the kinetics of the reaction of opening epoxides 1 by amines is modified so as to make the reaction selective toward one of the two epoxides.

This type of kinetic resolution is obtainable also with other nitrogen nucleophiles, such as ammonia, the azide ion ($N_3^-$), hydroxylamines.

The remaining epoxide and the product of the opening exhibit very different chemico-physical characteristics, allowing an easy separation thereof extractively, chromatographically or by crystallization.

Hence, object of the present invention is a process for the preparation of Nebivolol, the process comprising:

a. reacting the epoxide mixture 1 (RS, SR, RR and SS) of formula

Scheme 4

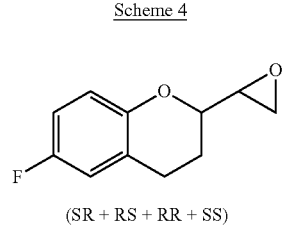

(SR + RS + RR + SS)    1 with an amine R—NH₂, wherein:

R is a protective group selected from methyl, allyl, t-butyl, benzyl, diphenylmethyl, triphenylmethyl, fluorenyl, 9,10-dihydroanthracen-9-yl, dibenzyl, wherein the aromatic rings present in the groups can be possibly mono- or disubstituted with a group selected from: halogen, nitro, a C1-C4 alkyl chain, CF₃, CHF₂, an OR₂ group, where R₂ is a hydrogen, a C1-C4 alkyl; and preferably a benzyl group, in a suitable solvent represented by a sterically hindered alcohol, alone or in mixture with an apolar solvent, to obtain a mixture of the four compounds 2, 3, 4 and 5, from which the pair 2/3 is separated from the pair 4/5;

Scheme 5

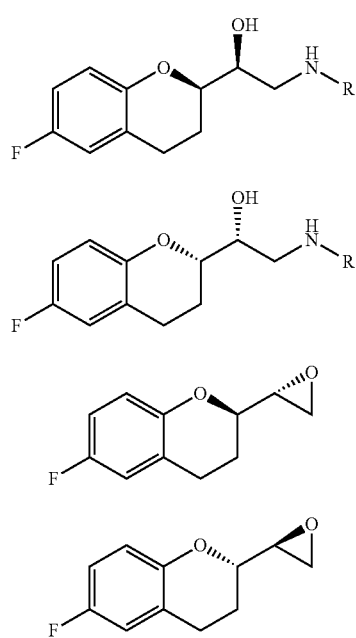

b. reacting the amines 2 and 3, in mixture, with the pair of epoxides 4 and 5, in mixture, to obtain a mixture of 4 compounds (6, 7, 8 and 9);

Scheme 6

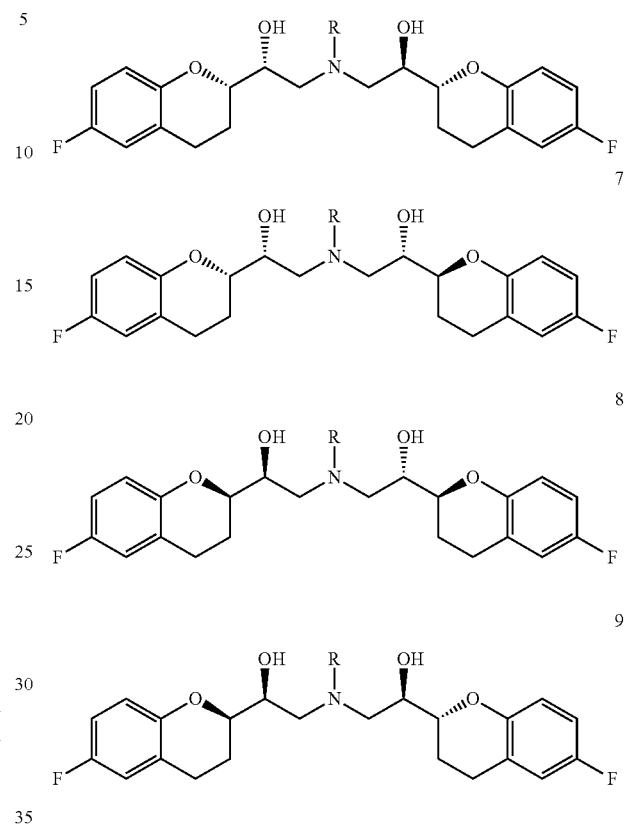

c. separating 6 and 8 (RSSS+SRRR) in mixture from 7 and 9 by fractional crystallization, by a first solvent selected from ethanol, propanol, isopropanol, tert-butanol, 2-methyl-2-butanol (preferably 2-methyl-2-butanol) and subsequently by a mixture between a polar aprotic solvent selected from ethyl acetate, methyl acetate, isopropyl acetate, acetone, methyl ethyl ketone, and an apolar solvent selected from pentane, hexane, cyclohexane, methylcyclohexane, heptane, benzene, toluene (preferably an ethyl acetate/cyclohexane mixture).

d. removing the protecting group R, with concomitant or subsequent forming of the hydrochloride salt.

As an alternative, the reaction described at point a. can be carried out by:

Scheme 7

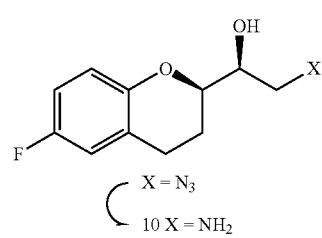

-continued

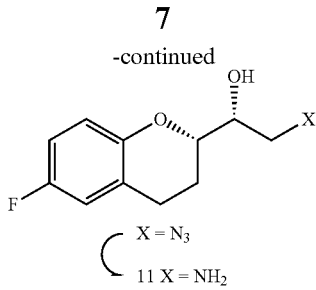

e. reacting the epoxide mixture 1 with ammonia or the azide ion, followed, in the case of azide, by reduction (Scheme 7);
f. separating the primary amine from the epoxides 4/5 by extraction in a suitable solvent or by chromatography;
g. carrying out a reductive amination of the amines 10/11 with an aldehyde $R_1CHO$, wherein $R_1$ is H, vinyl, phenyl, phenyl mono- or disubstituted with a group selected from: halogen, nitro, C1-C4 alkyl chain, $CF_3$, $CHF_2$, $OR_2$, where $R_2$ is a hydrogen, a C1-C4 alkyl; preferably phenyl, to obtain the mixture of amines 2/3;

Or, as an alternative to the reaction described at point e.:
h. reacting the epoxide mixture 1 with hydroxylamines, followed by N—O bond hydrogenation to produce amines 10/11.

A specific solution of the present invention is a process analogous to that described above, in which, as a partial alternative to point a., after reacting the amine $RNH_2$ with the epoxide mixture 1, the pair of compounds 2/3 is not separated from compounds 4/5, but:
k. excess of unreacted amine $RNH_2$ is removed
i. an alcoholic solvent selected from methanol or ethanol is added, and the compounds are left to react as envisaged at point b.

Another specific solution of the present invention is a process analogous to the above-described one in which, always as an alternative to point a.:
m. the reaction is had with a secondary amine of $RR_3NH$ type, wherein R has the meaning seen in the foregoing, and $R_3$ is a benzyl group, possibly mono- or disubstituted with a group selected from : halogen, nitro, a C1-C4 alkyl chain, $CF_3$, $CHF_2$, an $OR_2$ group, where $R_2$ is a hydrogen, a C1-C4 alkyl, and preferably a benzyl group, to obtain a mixture of the four compounds 12, 13, 4 and 5, from which the pair 12/13 is separated from the pair 4/5;

Scheme 8

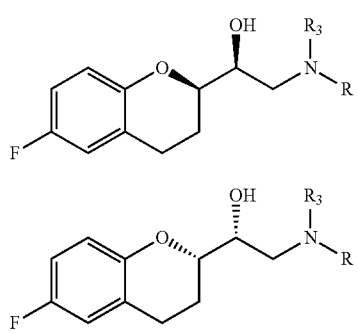

-continued

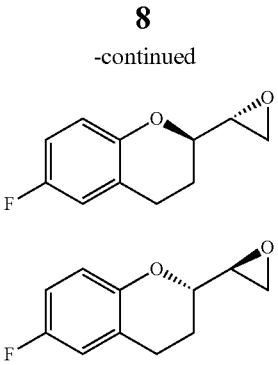

n. deprotecting from group $R_3$, to obtain a mixture of the compounds 2/3.

DETAILED DESCRIPTION OF THE INVENTION

According to the present invention the nebivolol compound is obtained with the method described in Scheme 1 starting from the mixture of the four isomers SR, RS, RR and SS of the epoxide of formula (1)

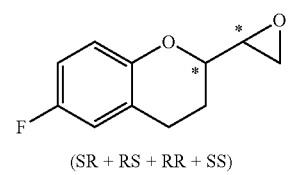

(SR + RS + RR + SS)

The epoxide mixture 1 is dissolved in a sterically hindered alcohol selected from iPrOH (isopropanol), sec-BuOH, tert-BuOH, isoamyl, 2-methyl-2-butanol, 2-methyl-2-pentanol, preferably an alcohol selected from: 2-methyl-2-butanol, tert-BuOH, and 2-methyl-2-pentanol, used alone or containing a variable amount of an apolar solvent selected from the group: petroleum ether, pentane, hexane, cyclohexane, methylcyclohexane, heptane, benzene, toluene, preferentially cyclohexane, in the ratio alcohol: apolar solvent of 1:1 to 10:1.

The solution is maintained at a temperature comprised between −20° and 60° C., preferably between 0° C. and 40° C., and even more preferably at 25° C. and additioned with an amine R—$NH_2$, where:
R is a protecting group selected from methyl, allyl, t-butyl, benzyl, diphenylmethyl, triphenylmethyl, fluorenyl, 9,10-dihydroanthracen-9-yl, dibenzyl, wherein the aromatic rings can be possibly mono- or disubstituted with a group selected from: halogen, nitro, a C1-C4 alkyl chain, $CF_3$, $CHF_2$, a group $OR_2$, where $R_2$ is a hydrogen, a C1-C4 alkyl; and preferably a benzyl group, in an amount of 1 to 10 equivalents, preferably 2 to 3 equivalents calculated with respect to the RS/SR epoxide mixture of formula 1.

The mixture thus obtained is stirred for 10-40 hours and preferentially for 12 hours. The precipitate formed (a mixture of compounds 2 and 3) is filtered off. The remaining solution is diluted with an apolar solvent selected from the group: petroleum ether, pentane, hexane, cyclohexane, methylcyclohexane, heptane, benzene, toluene, preferentially cyclohexane, in an amount that may range from 1 to 40 volumes, and washed with an aqueous acid solution (preferably $NaHSO_4$ or $NaH_2PO_4$). The organic phase, containing epoxides 4 and 5, is concentrated.

Amounts of the mixtures of compounds 2/3 and 4/5 are reacted in a ratio ranging from 0.7:1 to 1:0.7, and preferentially in an equimolar amount, in an inert organic solvent, like an aromatic hydrocarbon, a low molecular weight alcohol such as methanol, ethanol, isopropanol, butanol, a ketone, an ether or a polar aprotic solvent, preferentially ethanol (as reported in U.S. Pat. No. 4,654,362). The mixture, maintained at a temperature comprised between 40° C. and 120° C., preferentially between 50° C. and 90° C., is mixed to completion of the reaction; then, the solvent is evaporated.

The residue thus obtained is crystallized from an alcohol selected from ethanol, propanol, isopropanol, tert-butanol, 2-methyl-2-butanol, preferably 2-methyl-2-butanol, and subsequently from a mixture between a polar aprotic solvent selected from ethyl acetate, methyl acetate, isopropyl acetate, acetone, methyl ethyl ketone, and an apolar solvent selected from pentane, hexane, cyclohexane, methylcyclohexane, heptane, benzene, toluene; preferably a ethyl acetate/cyclohexane mixture, until reaching a >99% purity in the pair 6/8.

The compounds of formula 6/8 thus obtained, in case R is a benzyl group, are converted into nebivolol free base by hydrogenolysis with methods known to a person skilled in the art, and with a catalyst selected from Pd/C, Pd(OH)$_2$/C. Among those, the use of Pd(OH)$_2$ is preferable, as it offers advantages related to final product purity and reaction velocity. In case R is one of the other groups envisaged, deprotections are carried out by methods known in the state of the art; e.g., in case R=methyl, deprotection can be carried out photochemically, as described in Tetrahedron Letters (1989) 3977, for R=allyl, a catalytic hydrogenation can be done with a Pd-based catalyst, for R=t.butyl a treatment with methanol and hydrochloric acid is carried out, as described in J. Org. Chem. (2002), 8928-8937.

The nebivolol free base is converted into its hydrochloride salt after dissolution in ethanol according to methods known to a person skilled in the art (WO 95/22325).

In an alternative embodiment of the present invention, intermediates 2 and 3 are produced through steps (e) and (g). The SR, RS, RR and SS epoxide mixture 1 is reacted in an alcohol sterically hindered as seen in the foregoing, with ammonia or an azide, preferably sodium azide, at a temperature comprised between −20° and 60° C., preferably between 0° C. and 40° C. and even more preferably at 25° C. In case the azide is used, the reaction is followed by an intermediate reaction according to methods known in the state of the art, preferably by catalytic hydrogenation with a Pd/C or Pd(OH)$_2$/C type catalyst, with obtainment of the corresponding primary amine according to the following scheme (7):

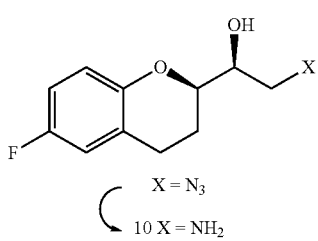

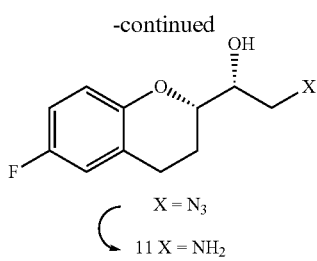

Then, primary amine is separated from epoxides 4/5 by extraction in a suitable solvent or by chromatography. Finally, a reductive amination of amines 10/11 is performed with an aldehyde R$_1$CHO, wherein R$_1$ is selected from the group: H, vinyl, phenyl, phenyl mono- or disubstituted with a group selected from: halogen, nitro, C1-C4 alkyl chain, CF$_3$, CHF$_2$, OR$_2$, where R$_2$ is a hydrogen, a C1-C4 alkyl, according to methods known in the art, typically with a borohydride. Thus, the mixture of amines 2/3 is obtained.

In another alternative embodiment of the invention, the SR, RS, RR and SS epoxide mixture 1 is reacted with hydroxylamine followed by N—O bond hydrogenation according to methods known in the art, typically by catalytic hydrogenation with a Pd-based catalyst, with obtainment of amines 10 and 11, which are then subjected to reductive amination, as described above, with an aldehyde R$_1$CHO and a borohydride, such as sodium borohydride, lithium borohydride, sodium cyanoborohydride, triacetoxysodium borohydride.

In another different embodiment, the pair of compounds 2 and 3 is not separated from compounds 4 and 5, but, after removal of the unreacted excess of amine RNH$_2$ and addition of a suitable solvent, the compounds 2 and 3 are left to react with the compounds 4 and 5 as already described above, directly obtaining the mixture of compounds 6, 7, 8 and 9. The suitable solvent added to the mixture is an alcoholic solvent, selected e.g. from methanol and ethanol.

The process of the invention can also be carried out according to a further variant, according to which the SR, RS, RR and SS mixture of the epoxide 1 is reacted, always in a sterically hindered alcohol analogously to what described in synthetic step a., with a secondary amine of RR$_3$NH type, wherein R has the meaning seen in the foregoing, and R$_3$ is a benzyl group, possibly mono- or disubstituted with a group selected from halogen, nitro, a C1-C4 alkyl chain, CF$_3$, CHF$_2$, an OR$_2$ group, where R$_2$ is a hydrogen, a C1-C4 alkyl, to obtain a mixture of the four compounds 12, 13, 4 and 5, from which the pair 12/13 is separated from the pair 4/5.

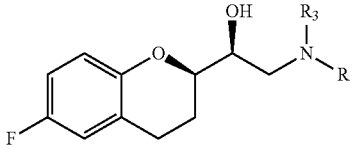

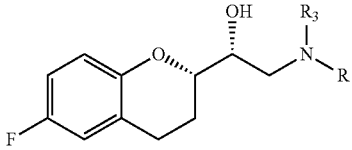

-continued

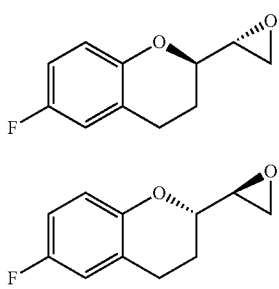

Finally, a deprotonation from group $R_3$ is performed, with obtainment of the mixture of the compounds 2/3. Deprotonation from group $R_3$ may be performed with known procedures, e.g. through catalytic hydrogenation with a known catalyst such as Pd/C or Pd(OH)$_2$/C.

EXAMPLES

The invention is hereinafter described in detail by the following examples, purely by way of illustration and not for imitative purposes, and with reference to scheme 9 herebelow:

Scheme 9

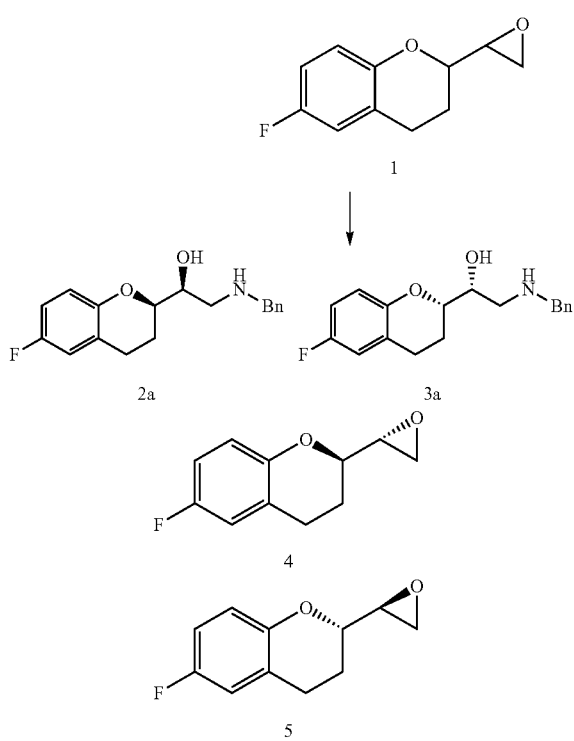

Example 1

Opening of epoxides 1 with benzylamine in 2-methyl-2-butanol

The diastereometric mixture of (RR/SS)- and (RS/SR)-6-fluoro-2-(oxiran-2-yl)chroman (mixture 1) (50 g, 88%, 226.8 mmol, epoxides ratio≈1:1) is placed in the reaction vessel and dissolved in 2-methyl-2-butanol (420 mL). Benzylamine (42.5 mL, 352.9 mmol) is added in one time to the solution under stirring. The solution is kept under stirring for 12 hours. At the end of the reaction, the amine 2a/3a formed is filtered under vacuum and dried (purity 96.2% 18.2 g, 57.9 mmol). The filtered solution is washed with 1M NaHSO$_4$ and H$_2$O (200 mL×3) to pH=5-6 and then concentrated under reduced pressure to ¼ of the volume (110 mL). To the mixture thus obtained, cyclohexane (420 mL, equal to the initial volume of the reaction) is added under brisk stirring. The solution is then filtered, dried (Na$_2$SO$_4$) and concentrated to obtain 18.4 g (purity 80%, 74.2 mmol, 65%) of mixture 4/5.

The amines deriving from the opening of epoxides 4/5 with benzylamine are formed in very low percentages and eliminated with the acid washing of the organic solution.

The identity and purity of the compounds obtained is evaluated by comparison with reference standards by HPLC, using a Merck Symmetry C-8 chiral column, 5 δm, 250×4.6 mm, and a suitable binary gradient.

Mixture 2a/3a: 1H-NMR (400 MHz, DMSO-d$_6$, δ): 7.31 (5H, m); 6.88 (2H, m); 6.68 (1H, m); 4.99 (brs, 1H), 3.88 (1H, m); 3.73 (2H, m); 3.66 (1H, m); 2.73 (2H, m); 2.73 (1H, m); 2.58 (1H, m); 2.10 (1H, br); 2.03 (1H, m); 1.68 (1H, m). MS: calcd for $C_{18}H_{20}FNO_2$ 301.1, found: 302.1

Mixture 4/5: 1H-NMR (400 MHz, DMSO-d$_6$, δ): 1.80 (1 H, m), 2.00 (1 H, m), 2.65-2.85 (4H, m), 3.15 (1H), 3.75 (2H, m), 6.80 (1H, m), 6.90 (2H, m MS (m/z): calcd. for $C_{11}H_{11}FO_2$ 194.1; found 236.5 [M+H$^+$+MeCN]$^+$; 194.5 [M]$^+$.

Example 2

Opening of epoxides 1 with benzylamine in 2-methyl-2-butanol/cyclohexane Mixture The mixture of epoxides 1 (10 g, purity 89.5%, 46.1 mmol) is dissolved in a 4:1 mixture of cyclohexane and 2-methyl-2-butanol (50 mL), benzylamine (8.5 mL, 7.65 mmol) is added and the mixture is mixed at room temperature. After about 10 hours a white precipitate is formed. After 38 hours a control by HPLC shows that the RS/SR epoxides pair has been completely consumed. The precipitate is filtered, obtaining 4.80 g of amine 2a/3a (purity: 99%, yield: 70%), while the filtrate is additioned with cyclohexane (40 mL).

This organic solution is washed with 1M NaHSO$_4$ (3×100 mL). During the first washing a yellow oil is separated from the solution (this oil contains possible dialkylation products and the amine of epoxides 4/5) and is eliminated. Then, it is washed with water (2×100 mL) to neutral pH, dried on Na$_2$SO$_4$, filtered and the solvent is removed under reduced pressure to obtain 3.70 g of mixture 4/5 (purity: 76%, yield: 83%).

The identity and purity of the compounds obtained is evaluated by comparison with reference standards by HPLC, using a Merck Symmetry C-8 chiral column, 5 urn, 250×4.6 mm, and a suitable binary gradient.

Comparison Example 3

Synthesis of Amines Deriving from the Pair of Epoxides 4/5

A sample of mixture 4/5 (0.5 g, 2.57 mmol), obtained by chromatographic purification of mixture 1, is dissolved in ethanol (5 mL) and additioned with benzylamine (0.84 mL, 7.72 mmol).

The mixture is heated to reflux until complete disappearance of the starting epoxides. The product is isolated by precipitation from the reaction mixture placed at 4° C.

¹H-NMR (DMSO-6d): 7.31 (5H, m); 6.88 (2H, m); 6.68 (1H, m); 4.85 (brs, 1H), 3.95 (1H, m); 3.73 (2H, s); 3.66 (1H, m); 2.75-2.60 (4H, m); 2.10 (1H, br); 1.90 (1H, m; 1.72 (1H, m).

Example 4

Reaction of Amines 2/3 with Epoxides 4/5

The compounds (±)-(RS/SR)-2-(Benzylamino)-1-(6-fluorochroman-2-yl)ethanol 2a/3a (18.26 g) and (±)-(RR/SS)-6-fluoro-2-(oxiran-2-yl)chroman 4/5 (18.4 g) are dissolved in absolute ethanol (60 mL) and maintained at reflux until disappearance of the starting reagents. At the end of the reaction the mixture is left to reach room temperature and the solvent is removed under reduced pressure. The residue is taken up in 2-methyl-2-butanol (150 mL, 4 vol) heated to dissolution (80° C.) and left at room temperature for 24 h under gentle stirring. The obtained solid is filtered, taking it up with 2-methyl-2-butanol (20 mL) and dried on a filter. The solid thus obtained (10.5 g) is suspended in cyclohexane/ethyl acetate 9/1 (100 mL, 10 vol) and heated to reflux until dissolution. It is then left to reach room temperature and the obtained solid is filtered, taking it up with cyclohexane (20 mL). It is dried on a filter, obtaining 9.80 g of mixture 6a/8a with purity higher than 99%. The compounds 7a/9a remained in the crystallization waters.

The identity and purity of the compounds is evaluated by comparison with reference standards by HPLC, using a Merck Symmetry C-8 chiral column, 5 μm, 250×4.6 mm, and a suitable binary gradient.

¹H-NMR (DMSO-6d): 7.33-7.19 (m, 5H), 6.90-6.72 (4H, m), 6.68-6.51 (m, 2H), 4.82 (d, 1H, J=3.0 Hz), 4.74 (1H, d, J=5.0 Hz), 4.00-3.90 (m, 1H), 3.87-3.70 (m, 4H), 3.53 (d, 1H, J=16.0 Hz), 2.83-2.40 (m, 8H), 1.90-1.70 (m, 2H), 1.68-1.50 (m, 2H).

MS (m/z): calcd. for $C_{29}H_{31}F_2NO_4$ 495.2; found 496.7 $[M+H]^+$.

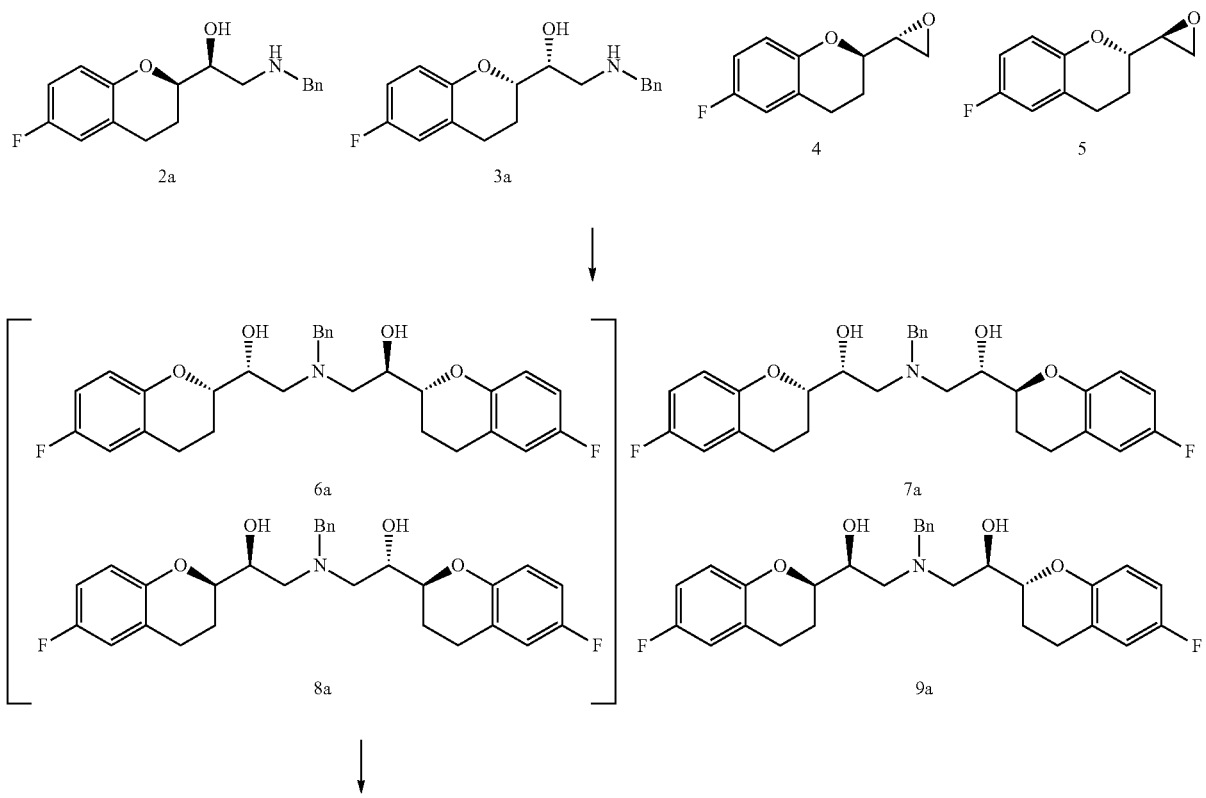

Scheme 10

Example 5

Removal of Protective Group

The mixture 6a/8a (4.00 g) is dissolved in EtOAc/absolute ethanol 1/4 (450 mL), and 20% Pd(OH)₂/C (50% wet, 200 mg) is added to the solution, under inert atmosphere (N₂). The mixture is maintained under hydrogen atmosphere. Upon disappearance of the initial compound, the mixture is filtered on celite or on material suitable for the purpose, washing it with the reaction mixture (50 mL). The solvents are removed under reduced pressure, obtaining a white solid residue (3.30 g) utilized as such in the subsequent step.

The identity and purity of the compounds is evaluated by comparison with reference standards by HPLC, using a Merck Symmetry C-8 chiral column, 5 μm, 250×4.6 mm, and a suitable binary gradient.

$^1$H-NMR (DMSO-6d): 6.92-6.82 (4H, m), 6.75-6.65 (m, 2H), 5.00 (d, 1H), 4.85 (1H, d), 3.98-3.82 (m, 2H), 3.70-3.60 (m, 2H), 2.85-2.60 (m, 8H), 2.10-2.00 (m, 1H), 1.98-1.82 (m, 1H), 1.80-1.60 (m, 2H).

MS (m/z): calcd. for $C_{22}H_{25}F_2NO_4$ 405.2; found 406.6 $[M+H]^+$.

Example 6

Salification of Nebivolol

Nebivolol free base (3.30 g, 8.70 mmol) is suspended in absolute ethanol (100 mL) and heated to fall until complete dissolution. To this solution, 1.25 M ethanolic HCl (7.5 mL) is added. The obtained solution is concentrated under reduced pressure, until obtaining a 15% concentration of the product. During solvent evaporation, progressive formation of a white precipitate is observed. The solid is filtered by washing with cold absolute ethanol, to obtain 3.10 g of nebivolol hydrochloride salt.

The chiral purity of the product and the ratio between the two enantiomers is evaluated by comparison with reference standards, by HPLC with an AKZO NOBEL column, Kromasil 5-AmyCoat, 5 μm, 250 mm×4.6 and a suitable binary gradient.

$^1$H-NMR (DMSO-6d): 8.66 (brs, 2H), 6.96-6.85 (m, 4H), 6.80-6.70 (2H, m), 5.96 (d, 1H, J=5.0 Hz), 5.77 (d, 1H, J=5.0 Hz), 4.12-4.06 (1H, m), 4.05-3.93 (m, 2H), 3.92-3.86 (m, 1H), 3.40-3.28 (m, 1H), 3.27-3.10(m, 2H), 3.00 (t, 1H, J=6.0 Hz), 2.90-2.68 (m, 4H), 2.15-2.05 (m, 1H), 1.95-1.85 (m, 1H), 1.80-1.60 (m, 2H).

MS (m/z): calcd. for $C_{22}H_{25}F_2NO_4$ 405.2; found 406.6 $[M+H]^+$.

Example 7

Opening of Epoxides 1 with Sodium Azide

A mixture of epoxides 1 (200 mg, 1.03 mmol) and sodium azide (100 mg, 1.5 mmol) in teramyl alcohol (2 mL) is additioned of DMF dropwise until complete solubilization. The solution thus obtained is mixed at room temperature until complete disappearance of the pair of RS/SR epoxides. Then, the mixture is washed with water (5×) and dried on sodium sulphate; it is filtered, the solvents are evaporated under reduced pressure and the residue is purified by flash chromatography, obtaining 90 mg (73%) of the pair of azides deriving from RS/SR epoxides (Scheme 7, X=N$_3$) and 80 mg of the pair 4/5. MS (m/z): calcd. for $C_{11}H_{12}FN_3O_2$ 237.0; found 238.1 $[M+H]^+$.

Example 8

Azide Reduction and Reductive Amination

A solution of the azides deriving form the opening of the RS/SR epoxides (90 mg, 0.38 mmol) is subjected to catalytic hydrogenation in EtOH and in the presence of 5% Pd/C. The solution thus obtained is filtered and additioned with benzaldehyde (40 mg, 0.38 mmol) and triacetoxysodium borhydride (90 mg, 0.41 mmol). At the end of the reaction the solvents are distilled at reduced pressure and the residue is taken up with dichloromethane and washed with 5% Na$_2$CO$_3$, followed by anhydrification on sodium sulphate. A chromatographic purification of the residue thus obtained yields 68 mg (60%) of the mixture of amines 2a/3a.

Example 9

Opening of Epoxides 1 with Benzylhydroxylamine

A mixture of epoxides 1 (200 mg, 1.03 mmol) and O-benzylhydroxylamine (184 mg, 1.5 mmol, from commercial hydrochloride salt) in teramyl alcohol (3 mL) is additioned with DMF dropwise until complete solubilization. The solution thus obtained is mixed at room temperature until disappearance of the RS/SR epoxides. Then, the mixture is washed with water (5×) and thereafter dried on sodium sulphate. It is filtered, solvents are evaporated under reduced pressure and the residue is purified by flash chromatography, obtaining 103 mg (65%) of the pair of hydroxylamines deriving from the RS/SR epoxides and 75 mg of the pair 4/5.

MS (m/z): calcd. for $C_{18}H_{20}F_2NO_3$ 317.1; found 318.2 $[M+H]^+$.

By treatment analogously to what reported in Example 8, the pair of hydroxylamines thus obtained is converted into the amines 2a/3a.

Example 10

Opening of RS/SR Epoxides with t-butylamine and Reaction In Situ with Epoxides 4/5

To a mixture of epoxides 1 (500 mg, 85%, 2.2 mmol) in teramyl alcohol (5 mL) terbutylamine (0.34 mL, 3.28 mmol) is added and the mixture is mixed until disappearance of the mixture of RS/SR epoxides. The solution is washed with 0.01N NaHSO$_4$ (4×) to remove excess terbutylamine, additioned with ethanol (2 mL) and heated to reflux until disappearance of the pair of epoxides 3/4. The solvents are distilled under reduced pressure, and the residue purified by flash chromatography to obtain the mixture of compounds 6-9, wherein R=tert-butyl (363 mg, 72%).

MS (m/z): calcd. for $C_{27}H_{35}F_2NO_3$ 459.3; found 460.4 $[M+H]^+$.

Example 11

Opening of the Epoxydes with Dibenzylamine and Selective Deprotection of a Benzyl A solution of the epoxydes 1 (100 mg, 0.51 mmol), dibenzylamine (150 μL., 0.70 mmol) in teramyl alcohol (1 mL) is mixed at room temperature, until disappearance of the RS/SR epoxides. Then, the crude product of the reaction is purified by flash chromatography, obtaining 63 mg (63%) of the amine mixture deriving from the opening of the RS/SR epoxydes with dibenzylamine and 51 mg (65%) of the pair of epoxides 4/5.

The dibenzylamine mixture is dissolved in ethanol (5mL) and hydrogenated with 5% Pd/C to obtain the benzylamines 2a/3a as main products (29 mg, 74%).

Example 12

Opening of the Epoxides with Dibenzylamine and Selective Deprotection of a Benzyl To a solution of the epoxides 1 (5 g, 25.7 mmol) in teramyl alcohol (45 ml), dibenzylamine (2.5 mL, 13.0 mmol, 0.5 eq)

was added and the mixture was stirred at room temperature until 5% of the RS/SR epoxides was left. Then the crude product of the reaction was purified by flash chromatography obtaining 3.5 g (9.0 mmol, 70%) of the amine mixture deriving from the opening with dibenzylamine of the RS/SR diastereomeric pair of epoxides 1 and 1.8 g (9.2 mmol, 72%) of the RR/SS pair of epoxides 4/5.

The dibenzylamine mixture (3.5 g, 9.0 mmol) was dissolved in absolute ethanol (35 ml, 10 V), and 114 mg of 10% Pd(OH)$_2$/C were added. The mixture was stirred under hydrogen atmosphere until disappearance of the starting compound (6 h) to obtain the benzylamines 2a/3a (2.2 g, 80%).

We claim:

1. A process for the preparation of the compound Nebivolol in the form of racemic mixture of the two enantiomers [2S [2R[R[R]]]] α,α'-[imino-bis (methylene)]bis[6-fluoro-chroman-2-methanol] and [2R[2S[S[S]]]] α,α'-[imino-bis (methylene)] bis[6-fluoro-chroman-2-methanol], having the following formulas

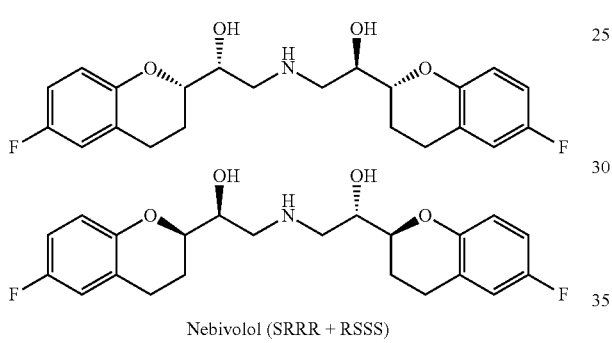

Nebivolol (SRRR + RSSS)

comprising the following steps:

a1. reacting a mixture of the four isomers SR, RS, RR and SS of the epoxide of formula (1)

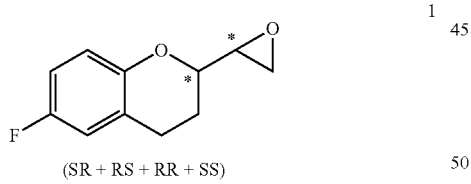

(SR + RS + RR + SS)

with an amine RR$_3$NH, wherein R and R$_3$ are benzyl groups, possibly each independently mono- or disubstituted with a group selected from the group consisting of: halogen, nitro, a C1-C4 alkyl chain, CF$_3$, CHF$_2$, and an OR$_2$ group, where R$_2$ is a hydrogen or C1-C4 alkyl, in a solvent represented by a sterically hindered alcohol selected from the group consisting of iPrOH, sec-BuOH, tert-BuOH, isoamyl, 2-methyl-2-butanol and 2-methyl-2-pentanol, used alone or in mixture with an apolar solvent selected from the group consisting of petroleum ether, pentane, hexane, cyclohexane, methylcyclohexane, heptane, benzene, and toluene, to obtain a mixture of the four compounds 12, 13, 4 and 5, from which the pair 12/13 is separated from the pair 4/5;

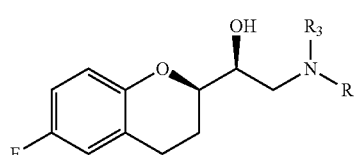

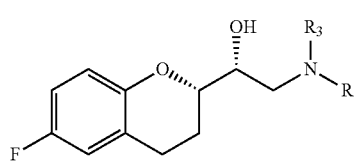

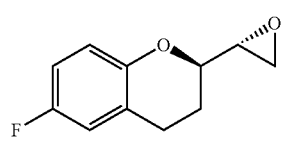

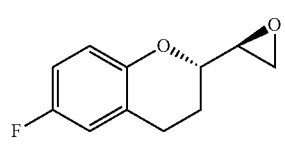

a2. eliminating the group R$_3$ to obtain a mixture of compound 2/3;

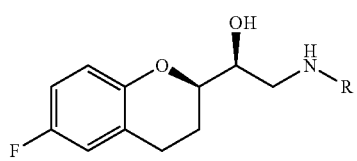

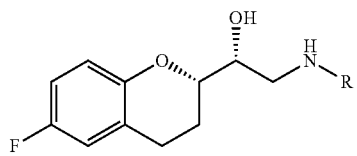

b. reacting the amines 2 and 3, in mixture, with the pair of epoxides 4 and 5, in mixture, to obtain a mixture of four compounds (6, 7, 8 and 9);

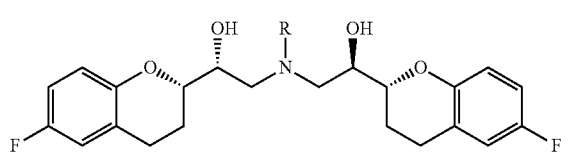

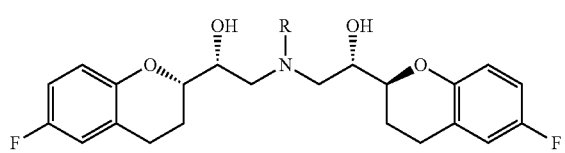

-continued

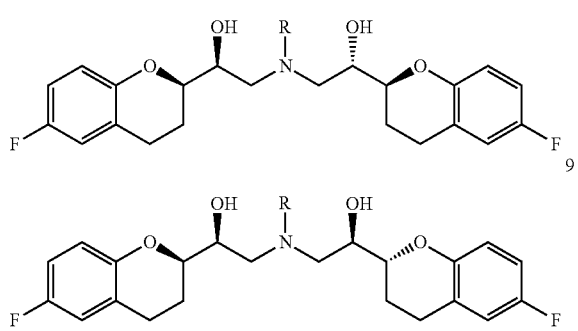

c. separating the compounds 6 and 8 (RSSS+SRRR), in mixture, from 7 and 9 by fractional crystallization, by a first solvent selected from the group consisting of ethanol, isopropanol, butanol, tert-butanol, and 2-methyl-2-butanol, and subsequently by a mixture of a polar aprotic solvent selected from the group consisting of methyl acetate, ethyl acetate, isopropyl acetate, acetone, methyl ethyl ketone, acetonitrile, and isopropyl ether, with an apolar solvent selected from the group consisting of pentane, hexane, cyclohexane, methylcyclohexane, heptane, benzene, and toluene; and d. removing the protecting group R, and optionally subsequently forming the hydrochloride salt, to obtain the final product Nebivolol or Nebivolol hydrochloride.

2. A process according to claim 1, wherein R and $R_3$ are each a benzyl group.

3. A process according to claim 2, wherein the amines 2 and 3 are separated from the epoxides 4 and 5 by precipitation and filtration.

4. A process according to claim 2, wherein the sterically hindered alcohol, defined at point a1, is selected from the group consisting of 2-methyl-2-butanol, tert-BuOH, and 2-methyl-2-pentanol.

5. A process according to claim 2, wherein the apolar solvent, defined at point a1, is cyclohexane.

6. A process according to claim 2, wherein the solvents for the fractional crystallization defined at point c are 2-methyl-2-butanol and subsequently an ethyl acetate/cyclohexane mixture.

7. A process according to claim 2, wherein the deprotecting envisaged at point d is performed by catalytic hydrogenation with $Pd(OH)_2$.

* * * * *